United States Patent [19]

Hotta et al.

[11] Patent Number: 4,510,089

[45] Date of Patent: Apr. 9, 1985

[54] OCTAHYDROTETRACYANOQUINODIMETHANE AND DERIVATIVES THEREOF

[75] Inventors: Shu Hotta, Hirakata; Tomiharu Hosaka, Yawata; Wataru Shimotsuma, Ibaraki, all of Japan

[73] Assignee: Matsushita Electric Industrial Company, Limited, Japan

[21] Appl. No.: 386,790

[22] Filed: Jun. 8, 1982

[30] Foreign Application Priority Data

Jun. 12, 1981 [JP] Japan .................. 56-91171
Jun. 12, 1981 [JP] Japan .................. 56-91172

[51] Int. Cl.³ ............................................. C07C 50/00
[52] U.S. Cl. ................................................ 260/396 N
[58] Field of Search ................................... 260/396 N

[56] References Cited

U.S. PATENT DOCUMENTS 3,162,641 12/1964 Acker et al. ............. 260/396 N X
3,687,987 8/1972 Martin ....................... 260/396 N

*Primary Examiner*—Delbert R. Phillips
*Attorney, Agent, or Firm*—Lowe, King, Price & Becker

[57] ABSTRACT

1,2,3,4,5,6,7,8-Octahydro-11,11,12,12-tetracyano-9,10-anthraquinodimethane compounds of the general formula

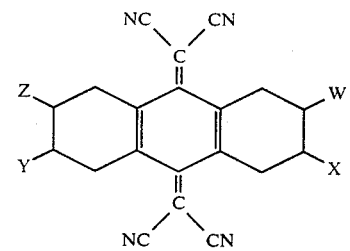

in which W, X, Y and Z independently represent hydrogen, halogen, hydroxyl group, hydrocarbon group having 1 to 8 carbon atoms, alkoxy group or acyloxy group provided that W=Y and X=Z, or W=Z and X=Y. The compositions and charge transfer complexes comprising these compounds are also described together with intermediates for the compounds.

7 Claims, 2 Drawing Figures

OCTAHYDROTETRACYANOQUINODIMETHANE AND DERIVATIVES THEREOF

BACKGROUND OF THE INVENTION

1. Field of the Invention

This invention relates to novel compounds and more particularly, to 1,2,3,4,5,6,7,8-octahydro-11,11,12,12-tetracyano-9,10-anthraquinodimethane and derivatives thereof and also to intermediates therefor.

7,7,8,8-tetracyanoquinodimethane (hereinafter abbreviated as TCNQ) and its derivatives are well known in the art as showing excellent semiconductive properties and are widely employed in electric or electronic and other industries.

The TCNQ has the chemical structure shown in the formula (1) below, in which the respective figures at the ring indicate the positions of carbon atoms. Derivatives of the TCNQ mean those compounds which have atoms other than hydrogen or atomic groups substituted for the hydrogen atoms joined at the 2-, 3-, 5- and 6-positions. Accordingly, the TCNQ derivatives have the skeletal structure of tetracyanoquinodimethane shown in the formula (2) and show excellent characteristics ascribed to this skeletal structure. It will be noted here that by the term "skeletal structure of tetracyanoquinodimethane" is meant a skeletal structure consisting of carbon atoms and nitrogen atoms constituting the TCNQ molecules.

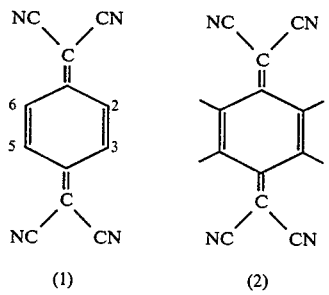

(1)  (2)

A number of references concerning TCNQ or its derivatives are known including, for example, D. S. Acker et al, J. Am. Chem. Soc., 84, 3370 (1962) and R. C. Wheland et al, J. Org, Chem., 40 (21), 3101 (1975) and the like.

SUMMARY OF THE INVENTION

An object of the present invention is to provide novel compounds which have the seletal structure of tetracyanoquinodimethane and have excellent chemical properties such as good solubility in solvents as well as excellent semiconductive characteristics.

Another object of the present invention is to provide hitherto unknown intermediates for those novel compounds.

A further object of the invention is to provide compositions and charge transfer complexes using the novel compounds.

According to one aspect of the present invention, there is provided a novel compound of the general formula (3), i.e. 1,2,3,4,5,6,7,8-octahydro-11,11,12,12-tetracyano-9,10-anthraquinodimethane (hereinafter abbreviated as HTCNAQ) or its derivative:

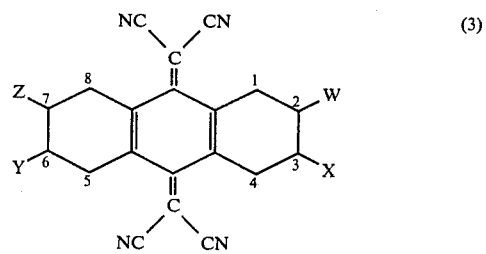

in which W, X, Y and Z are independently a hydrogen atom, a halogen atom, a hydroxyl group, a hydrocarbon group having 1 to 8 carbon atoms, an alkoxy group having 1 to 8 carbon atoms or an acyloxy group having 1 to 8 carbon atoms provided that $W=Y$ and $X=Z$ or $W=Z$ and $X=Y$. In the above formula, the figures show the positions of the individual carbon atoms.

Suitable selection of the substituents W, X, Y and Z permits formation of a variety of HTCNAQ derivatives having useful characteristics. These derivatives can be prepared from benzoquinone and butadiene or its various derivatives by a simple manner.

According to another aspect of the present invention, there is also provided a compound of the formula (4) which is obtained as an intermediate during the course of preparation of the above-indicated novel compounds:

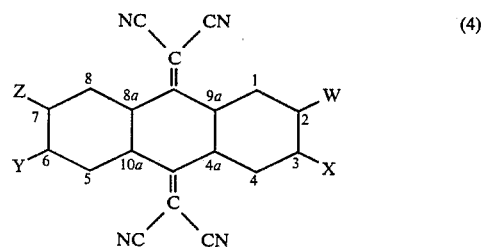

DETAILED DESCRIPTION OF THE INVENTION

Figure 1:
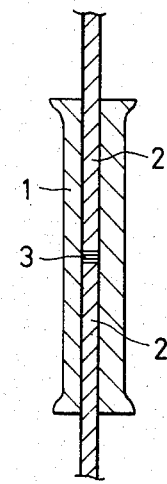
FIG. 1 is a schematic view, in longitudinal section, of a device for measuring the resistance of material.

As described above, in the formula (3), W, X, Y and Z are, respectively, hydrogen, halogen, hydroxyl group, hydrocarbon group containing 1 to 8 carbon atoms, alkoxy group having 1 to 8 carbon atoms or acyloxy group having 1 to 8 carbon atoms provided that $W=Y$ and $W=Z$ or $W=Z$ and $X=Y$. In addition, all of W, X, Y and Z may be the same atom or group. The hydrocarbon group having 1 to 8 carbon atoms includes an alkyl group such as methyl, ethyl, propyl, butyl, pentyl, hexyl, and octyl, or phenyl group or substituted phenyl group, and the like. The halgen atom is Cl, Br, or I. Examples of the alkoxy group are those which have 1 to 8 carbon atoms and include methoxy group, ethoxy group, butoxy group, pentoxy group, heptoxy group, hectoxy group, octoxy group, phenoxy group, and the like. Examples of the acyloxy group are also those having 1 to 8 carbon atoms and include acetoxy group through octanoyloxy groups, benzoyloxy group, benzylcarbonyloxy group and the like.

The HTCHQ and derivatives thereof are more particularly described in comparison with TCNQ and its derivatives obtained up to now.

The HTCNAQ and its derivatives of the present invention have the following characteristic fundamental structures.

(a) Skeletal structure of tetracyanoquinodimethane.

(b) Two substituted tetramethylene groups combined with the tetracyanoquinodimethane skeletal structure.

The HTCNAQ and its derivatives act as an organic seimconductor as discussed hereinafter and the semiconductive properties are characteristically dependent on the tetracyanoquinodimethane skeletal structure of (a). By the feature (b), the HTCNAQ and its derivatives are distinctly distinguished from TCNQ and conventionally employed TCNQ derivatives. This feature mainly contributes to produce useful effects of the invention such as an improvement in conductivity and ready solubility in solvent, so that the HTCNAQ and its derivatives become industrially useful as an organic compound or semiconductor.

The electric conductivity of HTCNAQ and its derivatives is approximately $1 \times 10^{-10}$ ohm$^{-1}$·cm$^{-1}$ which is high enough for use as an electronic material or a material for electronic parts. The reason for this is considered to result from the specific molecular structure of HTCNAQ or a derivative thereof. That is, in the molecule of the HTCNAQ derivatives, one substituted tetramethylene group is joined to each of the paired carbon atoms at 4a- and 9a-positions and at 8a- and 10a-positions, and these substituted tetramethylene groups have the ability of potentially passing or forcing electrons into the tetracyanoquinodimethane skeletal structure through the joining positions due to the hyperconjugation effect. By this, the width of energy between the normal or ground state and the excited state of the molecule is considered to become so small that the conductivity increases.

The HTCNAQ and its derivatives have good solubility in various solvents and this is why they have great merits from the industrial viewpoint. For instance, when polymeric compounds such as synthetic resins are treated on the surface thereof to lower the resistance of the surface, it is easy to control the degree of the surface treatment and the resistance by properly changing the concentration of a solution containing HTCHAQ or a derivative thereof. The good solubility is considered due to the relaxation of high polarity of the cyano groups owing to the two substituted tetramethylene groups.

The values of the solubility parameters (SP values) of HTCNAQ and its derivatives which were calculated from the attraction constant of molecules are shown in Table 1. The SP values were calculated from the following equation:

$$SP = \frac{d\Sigma G}{M}$$

in which
d: density of liquid or crystals
$\Sigma G$: sum of attraction constants of atomic groups in molecule
M: molecular weight In the table, 2,6-dimethyl-1,3,4,5,7,8-hexahydro-11,11,12,12-tetracyano-9,10-anthraquinodimethane is abbreviated, for example, as 2,6-dimethyl-HTCNAQ. This is true of other derivatives.

The alkyl substituents used are all linear.

TABLE 1

| Compounds | Density | ΣG | Molecular Weight | SP Value |
|---|---|---|---|---|
| Compounds of Invention | | | | |
| 2,6-dimethyl-HTCNAQ | 1.25 | 3074 | 340 | 11.3 |
| 2,7-dimethyl-HTCNAQ | 1.24 | 3074 | 340 | 11.2 |
| 2,3,6,7-tetramethyl-HTCNAQ | 1.27 | 3292 | 368 | 11.4 |
| 2,6-diethyl-HTCNAQ | 1.22 | 3606 | 396 | 11.1 |
| 2,6-dipropyl-HTCNAQ | 1.22 | 3606 | 396 | 11.1 |
| 2,6-dibutyl-HTCNAQ | 1.20 | 3872 | 424 | 11.0 |
| 2,6-dihexyl-HTCNAQ | 1.18 | 4404 | 480 | 10.8 |
| 2,6-dioctyl-HTCNAQ | 1.15 | 4936 | 536 | 10.6 |
| 2,6-diphenyl-HTCNAQ | 1.14 | 3794 | 464 | 9.3 |
| HTCNAQ | 1.31 | 2856 | 312 | 12.0 |
| Reference Compounds | | | | |
| TCNQ | 1.32 | 2160 | 204 | 14.0 |
| acetonitrile | 0.78 | 624 | 41 | 11.9 |
| propionitrile | 0.78 | 757 | 55 | 10.7 |
| benzonitrile | 1.01 | 982 | 103 | 9.6 |

For instance, good solutilities of 2,6-dihexyl HTCNAQ and 2,6-dioctyl HTCNAQ in propionitrile can be understood from the facts that the SP values of these derivatives are almost equal to that of propionitrile and that these derivatives and propionitrile commonly contain the cyano group therein. This is true of good solubility of 2,6-diphenyl HTCNAQ in benzonitrile.

HTCNAQ and its derivatives have also good miscibility with various typs of polymers. This is very advantageous in that compositions obtained by incorporating HTCHAQ derivatives in polymer matrice have very great usefulness and a wide range of applications. That is, the SP values of the HTCNAQ dertvatives of the invention are approximately within a range of from 9 to 11 and a wide variety of polymers have the SP values within the above range. Proper selection of a polymer compound depending on the type of the derivative will allow easy formation of a composition in which these ingredients are completely miscible with each other. This is particularly interesting in respect of electric characteristics. Where an HTCHAQ derivative is admixed with a polymeric compound showing good miscibility with the derivative such as by a kneading technique, the derivative is uniformly dispersed or dissolved in the polymer. Accordingly, the mixing with only a small amount of the derivative can improve and stabilize the conductivity of the composition. Additionally, a slight variation in mixing amount does give little influence on the conductivity. The good miscibility with polymeric compounds does not induce HTCHAQ and its derivatives to bleed out from the composition.

The preparation of HTCHAQ and its derivatives involves the following three steps in a broad aspect.

(a) p-Benzoquinone and butadiene with or without a mono-substituent at the 2-position or di-substituents at the 2,3-positions are provided as starting materials and subjected to the Diels-Alder reaction, followed by adding hydrogen to obtain a dodecahydro-9,10-anthraquinone.

(b) The thus obtained dodecahydro-9,10-anthraquinone is substituted at the oxygen atom of each ketone group with a dicyanomethylene group of the formula (5) to obtain dodecahydro-11,11,12,12-tetracyano-9,10- anthraquinodimethane or its derivative of the aforeindicated formula (4).

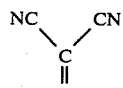

These compounds of the formula (4) are hitherto unknown and may have utility in preparation of specific types of compounds other than the final products of the present invention.

(c) Finally, dodecahydro-11,11,12,12-tetracyano-9,10-anthraquinodimethane or its derivative is partially dehydrogenated to obtain HTCHAQ or its derivative. The derivatives of HTCNAQ can be classified into three categories including 2,3,6,7-tetrasubstituted HTCNAQ products, 2,6-disubstituted HTCNAQ products and 2,7-disubstituted HTCNAQ products.

The general technique of introducing the dicyanomethylene group in (b) is used for synthesizing TCNQ and is particularly described, for example, in D. S. Acker et al, J. AM. Chem. Soc., 84, 3370 (1962).

In step (c), the hydrogen atoms joined to the carbon atoms at the 4a, 8a, 9a and 10a positions are more eliminable than the hydrogen atoms joined to the carbon atoms at 1 through 8 positions. This is because the electrons of the former hydrogen atoms commonly used with the joined carbon atoms are attracted through the double bond toward the tetracyanoquinodimethane skeletal structure by the potential electron-attracting force of the cyano group, and such hydrogen atoms are more eliminable as proton than the latter hydrogen atoms. Another factor is considered as follows: the double bonds established between the 4a and 9a positions and also the 8a and 10a positions are stabilized by the hyperconjugation effect. This effect is well known in the field of the organic synthetic chemistry as the Saytzeff rule. Accordingly, by selection of appropriately mild reaction conditions, the partical dehydrogenation reaction where the hydrogen atoms joined at the 4a, 8a, 9a and 10a positions are selectively eliminated is caused to proceed thereby selectively producing HTCNAQ or its derivative.

HTCNAQ and its derivatives can readily be purified to obtain highly pure crystals. Because of the above nature and the ready solubility in solvent, recrystallization operation is readily feasible for purification and thus an extremely high purity compound can be obtained if desired.

Use and application of HTCNAQ and its derivatives is described. Not only HTCNAQ and its derivatives themselves have wide utility in the field of electrical and electronic industries, but also they are usable as an intermediate for other useful compounds or materials. Furthermore, compositions of these HTCNAQ compounds or materials admixed with other inorganic compounds or organic compounds will show excellent characteristics. These compounds, materials or compositions may have wide applications as organic electronic materials. Use of these materials of the suitable types and forms depending on the spplication and use in end purpose will give favorable and satisfactory results.

Applications of the HTCNAQ and its derivatives as charge transfer complexes and compositions are briefly described below.

(1) Charge transfer complexes

Charge transfer complexes of HTCNAQ or its derivatives can be formed by doping compounds serving as an electron donor against HTCNAQ or its derivatives. These charge transfer complexes themselves are semiconductors of excellent characteristics and may be mixed with or dispersed in polymers to give compositions covering a wide range of electrical characteristics. The electron donors particularly useful in combination with the compounds of the invention include metal elements such as sodium, copper and the like, aromatic compounds such as anthracene, pyrene and the like, amino compounds and compounds having the phthalocyanine structure.

(2) Mixture or dispersion compositions

HTCNAQ compounds or charge transfer complexes derived from the HTCNAQ compounds may be mixed with one another or may be mixed with or dispersed in polymer matrice to obtain a diversity of mixtures of dispersions of desired levels of intended electrical or electronic characteristics. These compounds or charge transfer complexes or mixture or dispersion compositions have a wide variety of applications as organic electronic materials such as dielectric materials, conductors, resistors and thermister materials.

The present invention is described in more detail by way of an example of preparing HTCHAQ and its derivatives.

EXAMPLE

HTCNAQ and a number of derivatives thereof were prepared according to the following procedure.

(a) Synthesis of dodecahydro-9,10-anthraquinone and derivatives thereof

According to a series of the following reaction formulas, dodecahydro-9,10-anthraquinone and its derivatives of the formula (6) were prepared.

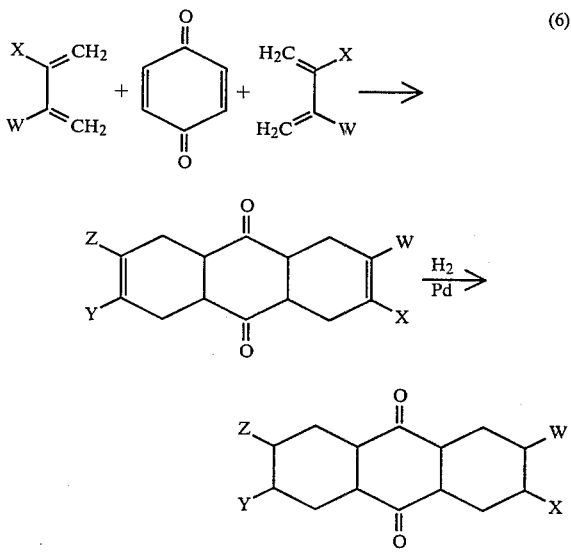

in which W, X Y and Z have the same meanings as defined hereinbefore. The butadiene derivatives used were 2-methylbutadiene, 2,3-dimethylbutadiene, 2-ethylbutadiene, 2,3-diethylbutadiene, 2-propylbutadiene, 2-butylbutadiene, 2-pentylbutadiene, 2-hexylbutadiene, 2-octylbutadiene, 2-phenylbutadiene, 2-(p-methylphenyl)butadiene, 2-chlorobutadiene, 2,3-dichlorobutadiene, 2-bromobutadiene, 2-hydroxybutadiene, 2,3-dihydroxybutadiene, 2-methoxybutadiene, 2,3-dimethoxybutadiene, 2-ethoxybutadiene, 2-phenoxybutadiene, 2-acetoxybutadiene, and 2-benzoyloxybutadiene. Butadiene was also used for the preparation of HTCNAQ.

The reaction was conducted using a solution of p-benzoquinone and each of the above-mentioned butadiene derivatives in benzene under heating and refluxing conditions for four hours. The resulting compounds were dissolved in ethanol, in which was suspended a palladium catalyst adsorbed on alumina. Thereafter, hydrogen gas was blown into the solution for 2 hours while keeping the temperature of the solution at 20° C. to obtain dodecahydro-9,10-anthraquinone derivatives.

(b) Synthesis of HTCNAQ and its derivatives 0.2 mole of each of the thus obtained dodecahydro-9,10-anthraquinone and its derivatives and 0.24 mole of malonitrile were dissolved in 200 ml of benzene, to which were added 12 ml of acetic acid and 4 ml of ammonium acetate, followed by refluxing with agitation for 3 hours. Then, the solution was coolded, filtered, and recrystallized from acetonitrile to obtain dodecahydro-11,11,12,12-tetracyano-9,10-anthraquinodimethane and its derivatives of the formula (5).

The yields more or less varied according to the type of the derivatives but were over 60% in all the cases.

0.1 mole of each of the compounds was charged together with 0.12 mole of bromine into 1000 ml of acetonitrile cooled to 0° C. and the reaction system was substituted with nitrogen gas. To the solution was further added 25 ml of alpha-picoline, which was agitated for 1 hour while keeping the solution at 0° C. and then cooled water was added so as to cause crystals to precipitate. After filtration, the crystals were recrystallized from acetonitrile to obtain HTCNAQ and its derivatives of the formula (3) shown hereinbefore.

Stereoisomers obtained from the starting butadiene derivatives other than butadiene, 2,3-dimethylbutadiene, 2,3-diethylbutadiene, 2,3-dichlorobutadiene, 2,3-dihydroxybutadiene and 2,3-dimethoxybutadiene were separated into 2,6-di-substituted products and 2,7-di-substituted products by the use of the ordinary paper chromatography. These isomers were identified by measurement of dipole moment where a compound whose dipole moment was zero was determined as the 2,6-disubstituted product.

In Table 2, the butadiene derivatives used and final HTCNAQ and its derivatives are summarized.

TABLE 2

| Butadiene Derivatives | | |
|---|---|---|
| W— | X— | HTCNAQ and Its Derivatives |
| H— | H— | HTCNAQ |
| H— | CH₃— | 2,6-dimethyl-HTCNAQ<br>2,7-dimethyl-HTCNAQ |
| CH₃— | CH₃— | 2,3,6,7-tetramethyl-HTCNAQ |
| H— | C₂H₅— | 2,6-diethyl-HTCNAQ<br>2,7-diethyl-HTCNAQ |
| C₂H₅— | C₂H₅— | 2,3,6,7-tetraethyl-HTCNAQ |
| H— | CH₃(CH₂)₂— | 2,6-dipropyl-HTCNAQ<br>2,7-dipropyl-HTCNAQ |
| H— | CH₃(CH₂)₃— | 2,6-dibutyl-HTCNAQ<br>2,7-dibutyl-HTCNAQ |
| H— | CH₃(CH₂)₄— | 2,6-dipentyl-HTCNAQ<br>2,7-dipentyl-HTCNAQ |
| H— | CH₃(CH₂)₅— | 2,6-dihexyl-HTCNAQ<br>2,7-dihexyl-HTCNAQ |
| H— | CH₃(CH₂)₇— | 2,6-dioctyl-HTCNAQ<br>2,7-dioctyl-HTCNAQ |
| H— | C₆H₅— | 2,6-diphenyl-HTCNAQ<br>2,7-diphenyl-HECNAQ |
| H— | CH₃-C₆H₄— | 2,6-bis(p-methylphenyl)-HTCNAQ<br>2,7-bis(p-methylphenyl)-HTCNAQ |
| H— | Cl— | 2,6-dichloro-HTCNAQ<br>2,7-dichloro-HTCNAQ |
| Cl— | Cl— | 2,3,6,7-tetrachloro-HTCNAQ |
| H— | Br— | 2,6-dibromo-HTCNAQ<br>2,7-dibromo-HTCNAQ |
| H— | OH— | 2,6-dihydroxy-HTCNAQ<br>2,7-dihydroxy-HTCNAQ |
| OH— | OH— | 2,3,6,7-tetrahydroxy-HTCNAQ |
| H— | CH₃O— | 2,6-dimethoxy-HTCNAQ<br>2,7-dimethoxy-HTCNAQ |
| CH₃O— | CH₃O— | 2,3,6,7-tetramethoxy-HTCNAQ |
| H— | CH₃CH₂— | 2,6-diethoxy-HTCNAQ<br>2,7-diethoxy-HTCNAQ |
| H— | C₆H₅-O— | 2,6-diphenoxy-HTCNAQ<br>2,7-diphenoxy-HTCNAQ |
| H— | CH₃COO— | 2,6-diacetoxy-HTCNAQ<br>2,7-diacetoxy-HTCNAQ |
| H— | C₆H₅-COO— | 2,6-dibenzoyloxy-HTCNAQ<br>2,7-dibenzoyloxy-HTCNAQ |

Note
W— and X— represent substituents of the butadiene derivative of the formula (6), respectively.

Figure 2:
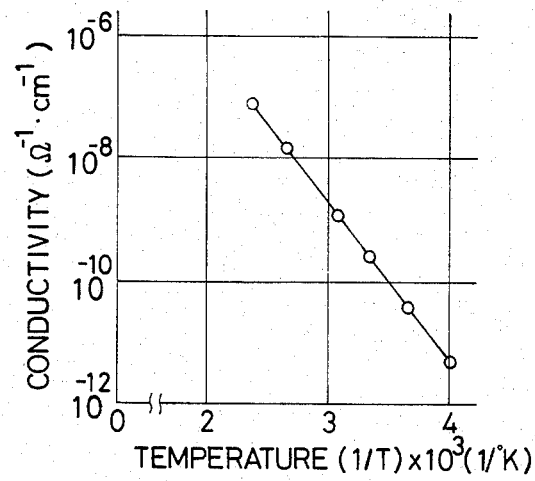
FIG. 2 is a graph showing the relation between the conductivity of a compressed powder sample of 2,6-dimethyl-1,3,4,5,7,8-hexahydro-11,11,12,12-tetracyano-9,10-anthraquinone and the temperature.

Each of these HTCNAQ derivatives in the form of crystals was dried and ground to pieces in a mortar, followed by drying in vacuo over day and night at 80° C. This powder was placed in a glass tube with an inner diameter of 1 mm as shown in FIG. 1 and stainless steel electrodes 2 each with an outer diameter of 1 mm were inserted from opposite ends of the glass tube 1. The electrodes were exerted with a load of 100 g to compress a powder 3 of the sample so that the length of the sample was 1 mm. The conductivity of the powder sample 3 was measured in relation to variation in temperature. The conductivities of all the samples were almost at the same level, i.e. about $1 \times 10^{-10}$ ohm$^{-1}$·cm$^{-1}$. FIG. 2 shows a graph showing the relation between the conductivity of 2,6-dimethyl-HTCNAQ and the temperature.

What is claimed is:

1. A compound of the general formula

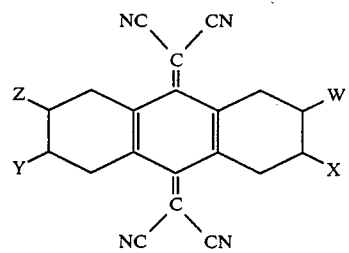

in which W, X, Y and Z independently represent hydrogen, halogen, hydroxyl group, hydrocarbon group having 1 to 8 carbon atoms, alkoxy group having 1 to 8 carbon atoms or acyloxy group having 1 to 8 carbon atoms provided that W=Y and X=Z or W=Z and X=Y.

2. 1,2,3,4,5,6,7,8-octahydro-11,11,12,12,-tetracyano-9,10,-anthraquinodimethane.

3. Derivatives of 1,2,3,4,5,6,7,8-octahydro-11,11,12,12-tetracyano-9,10-anthraquinodimethane of the general formula

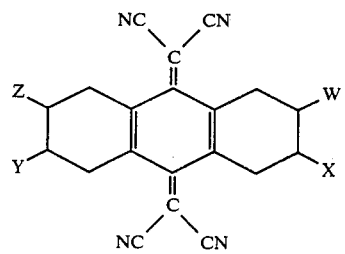

in which W, X, Y and Z independently represent hydrogen, halogen, hydroxyl group, hydrocarbon group having 1 to 8 carbon atoms, alkoxy group or acyloxy group provided that W=Y and X=Z or W=Z and X=Y and that X or W is an atom or group other than hydrogen.

4. The derivatives according to claim 3, wherein W=Y=X=Z.

5. The derivatives according to claim 4 being 2,3,6,7-tetra-substituted products.

6. The derivatives according to claim 3, wherein the derivatives are 2,6-di-substituted products or 2,7-di-substituted products.

7. The derivatives according to claim 3, wherein W represents hydrogen and X represents halogen, hydroxy group, hydrocarbon group having 1 to 8 carbon atoms, alkoxy group having 1 to 8 carbon atoms or acyloxy group having 1 to 8 carbon atoms.

* * * * *